US 6,589,176 B2

(12) United States Patent
Jago et al.

(10) Patent No.: US 6,589,176 B2
(45) Date of Patent: Jul. 8, 2003

(54) ULTRASONIC IMAGE STABILIZATION SYSTEM AND METHOD

(75) Inventors: James Jago, Seattle, WA (US); Lars Jonas Olsson, Woodinville, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/010,298

(22) Filed: Dec. 5, 2001

(65) Prior Publication Data

US 2003/0105401 A1 Jun. 5, 2003

(51) Int. Cl.$^7$ ................................................. A61B 8/00
(52) U.S. Cl. ...................................................... 600/443
(58) Field of Search ........................ 600/437, 440–447, 600/449–471; 73/625, 626; 367/7, 11, 87, 130, 138, 103, 105; 348/208, 142, 155, 700, 135, 169, 207, 209; 128/916; 342/81

(56) References Cited

U.S. PATENT DOCUMENTS

| 5,538,004 A | 7/1996 | Bamber |
| 5,566,674 A | 10/1996 | Weng |
| 5,575,286 A | 11/1996 | Weng et al. |
| 5,655,535 A | 8/1997 | Friemel et al. |
| 5,776,066 A | 7/1998 | Nock et al. |
| 5,782,766 A | 7/1998 | Weng et al. |
| 5,873,830 A | * 2/1999 | Hossack et al. ............. 600/447 |
| 5,973,733 A | * 10/1999 | Gove ..................... 348/208.13 |
| 6,095,976 A | * 8/2000 | Nachtomy et al. .......... 600/443 |

FOREIGN PATENT DOCUMENTS

EP          0 717 956 B1      2/2001

OTHER PUBLICATIONS

Jin et al., "A Stable Vision System for Moving Vehicles," IEEE Trans. of Intell. Transport. Systems, vol. 1, No. 1, Mar. 2000, pp. 32–39.
Ratakonda, "Real–Time Digital Video Stabilization for Multi–Media Applications," IEEE 1998, Univ. of Illinois, Dept. of Elec. and Comp. Engin., pp. IV=69–IV–72.

* cited by examiner

Primary Examiner—Marvin M. Lateef
Assistant Examiner—Ali M. Imam
(74) Attorney, Agent, or Firm—W. Brinton Yorks, Jr.

(57) ABSTRACT

An ultrasonic diagnostic imaging system is provided in which anatomical images are stabilized in the presence of probe motion, anatomical motion, or both. A decision processor analyzes motional effects and determines whether to inhibit or allow image stabilization. Images are anatomically aligned on the basis of probe motion sensing, image analysis, or both. The stabilization system can be activated either manually or automatically and adaptively.

29 Claims, 4 Drawing Sheets

| Condition | Stabilization Decision |
|---|---|
| Probe/anatomy moves large distance | Unlock |
| Probe/anatomy moves quickly | Unlock |
| Probe/anatomy moves slowly a short distance | Stay locked |
| Probe/anatomy moves slowly a long distance | Unlock |
| Few pixels in image move | Stay locked |
| Many pixels in image move | Unlock* |
| Low correlation coefficient | Unlock |

ULTRASONIC IMAGE STABILIZATION SYSTEM AND METHOD

This invention relates to ultrasonic diagnostic imaging systems and, in particular, to ultrasonic diagnostic imaging systems which produce images that are stabilized in the presence of probe or anatomical motion.

Ultrasonic diagnostic imaging systems enable the diagnosis of the anatomy of a patient by real time two and three dimensional imaging. The quality and resolution of ultrasonic images has become advanced to the point where physicians can locate and study even the smallest anatomical details, such as heart valve motion and flow characteristics in individual blood vessels. But motional effects can render such advances ineffective. For instance, a physician may be trying to image the kidney of an infant to assess the bloodflow perfusion in the organ. The infant, however, will not comprehend this procedure and may struggle and squirm as the physician attempts to hold the ultrasound system probe in steady contact with the infant's abdomen. The struggling of the infant can prevent any continuous steady probe contact, causing the anatomy in the image to jitter and move erratically as the probe moves involuntarily. The physician can attempt to overcome these circumstances by pressing the Freeze button to capture an image when she feels she has an adequate image of the kidney, but this can be a haphazard, hit-or-miss exercise. Under these conditions the physician may not be able to obtain images which enable a confident diagnosis.

Another example of deleterious motional effects even with a cooperative patient is cardiac imaging. A cardiologist may be imaging the heart and attempting to discern whether there are any jets or leaks from a heart valve. These effects can be very tiny in the image and may only appear momentarily when they are in the image plane or volume. However, as the heart beats it often does not do so in the same location, but can swing from side to side in the chest cavity. This movement of the entire organ can make focusing on a constant spot in the vicinity of a heart valve difficult. If the ultrasound system is being operated in the "zoom" mode in which an enlarged portion of a larger field of view is being observed, the anatomy of interest can move completely out of the zoom field of view due to this motion. Again, motion can prevent the acquisition of images needed for a confident diagnosis. In this case the motion is of anatomy in the body rather than the ultrasound probe. It would be desirable for the ultrasound system to ameliorate these motional problems automatically to better facilitate the acquisition of diagnostically valid images under difficult imaging circumstances.

In accordance with the principles of the present invention, an ultrasound system and method are provided for stabilizing images on a display screen in the presence of probe and/or anatomical motion. When the clinician is moving the probe in a survey mode in a search for specific anatomy, the system performs in the normal manner. But when the clinician is focusing attention on specific anatomy, the system stabilizes the anatomy being viewed on the display screen. This can be done either upon the command of the clinician or adaptively by the system. When in the stabilization mode the system will end efforts at image stabilization based upon operating conditions which reduce the utility of stabilization or indicate the clinician's desire to begin a survey mode of operation.

Figure 1:
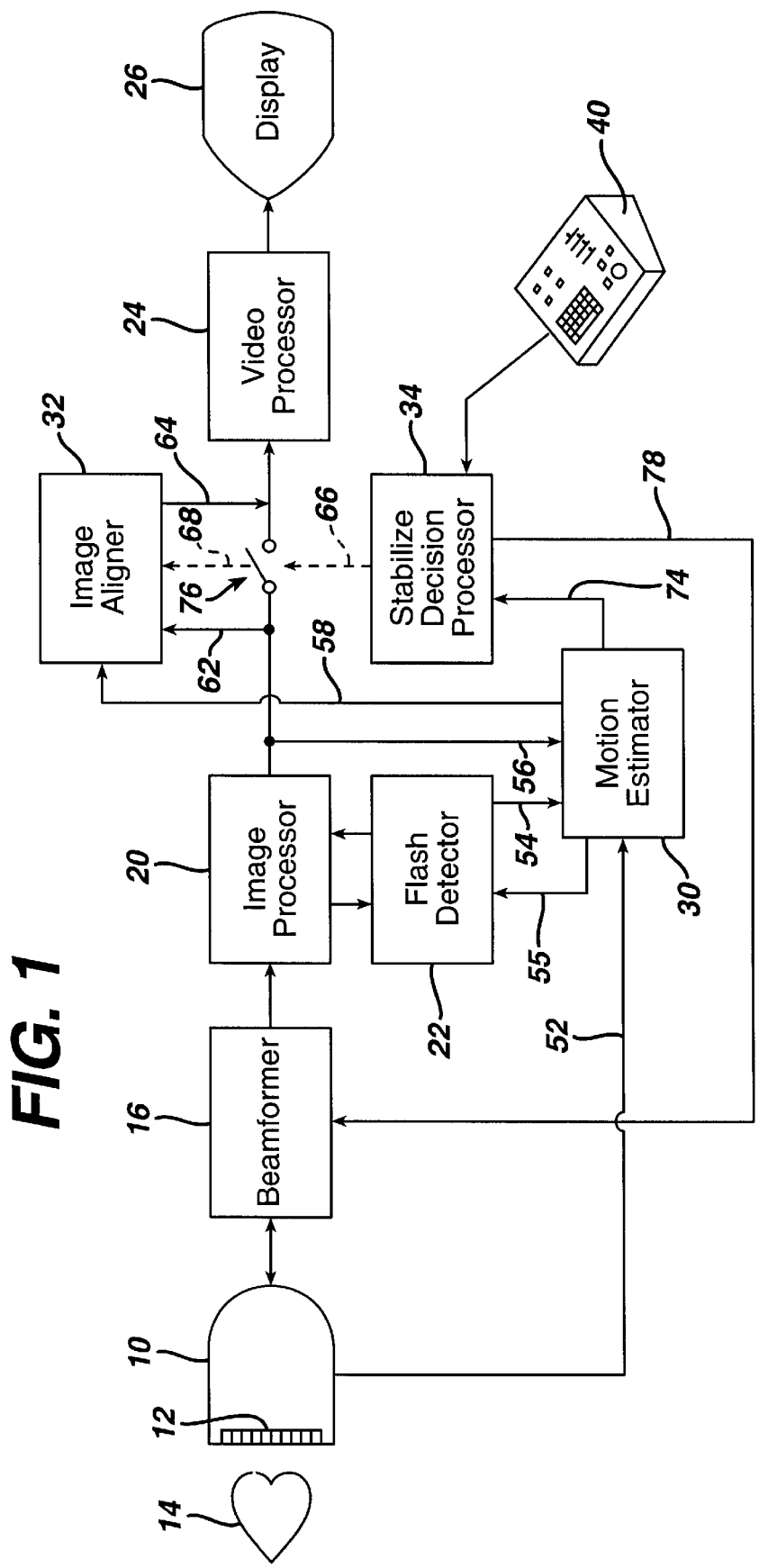
FIG. 1 illustrates in block diagram form an ultrasound system constructed in accordance with the principles of the present invention.

Referring first to FIG. 1, an ultrasound system constructed in accordance with the principles of the present invention is shown in block diagram form. A probe 10 including a transducer array 12 is used to scan the anatomy of a patient. The anatomy is symbolically represented in the drawing by the shape of a heart 14 in front of the aperture of the transducer array to indicate that the probe is scanning the heart as described in one of the following examples. The array transducer 12 can be either a one dimensional or a two dimensional array which scans a single plane or a volumetric region of a patient. The beams from the array can be steered electronically or mechanically by moving the array to scan the patient. The transmission of ultrasonic beams from the probe 10 and the processing of received echoes to form coherent echo signals is performed by a beamformer 16, which may form one or more received scanlines of an image in response to a transmit-receive sequence by the probe. The received scanline signals are then processed into the desired type of image by an image processor 20. The image processor may process the received echo signals to form fundamental or harmonic image signals, for instance, and may produce Doppler or B mode signals for display. Undesired signal or image components may be reduced or eliminated by the image processor 20. Motion artifacts such as unwanted flash artifacts can be detected by a flash detector 22, then removed by signal or image processing. Various techniques for detecting and suppressing flash are known, such as those shown in U.S. Pat. Nos. 5,197,477 and 5,782,769 for Doppler flash, and U.S. patent application Ser. No. 09/693,059, filed Oct. 20, 2000 for harmonic separation flash artifacts. The image processor also performs image formation operations such as scan conversion. In a standard ultrasound system the image signals are coupled to a video processor 24 which converts the image signals into display signals suitable for driving an image display 26.

In accordance with the principles of the present invention a motion estimator 30 is provided which is capable of estimating several kinds of motional effects. Motional effects which can affect the stability of an ultrasound image include probe motion and motion of the anatomy being imaged. The motion estimator 30 estimates motional effects from one or both of these sources. For instance, the probe 10 may include motional sensors which provide an indication of probe motion to the motion estimator 30, such as the inertial sensors of acceleration described in U.S. Pat. No. 5,529,070. Optical or mechanical sensors may also be used in the probe to sense probe motion. Signals from these sensors are coupled to the motion estimator 30 over line 52 in the system of FIG. 1. The motion artifacts which cause flash can result from either probe or anatomical motion, and these sensations of motion are coupled to the motion estimator 30 over line 54. Estimated motion can also be coupled back to the flash detector 22 over line 55 to improve the effectiveness of flash suppression. Doppler signals can also be used to detect probe motion as described in U.S. Pat. No. 5,127,409 and are coupled to the motion estimator 30 over either line 54 or line 56.

Anatomical or probe motion will also manifest itself in the ultrasound image by a displacement of anatomy in the image from one image frame to another. This motion can be estimated by image processing in which the signal or image content of one frame is compared with another image frame acquired at a different point in time. Techniques which can be used for motion detection in images include feature matching, mutual information, correlation, normalized correlation, r.f. correlation in the axial direction of a scanline, or minimum sum-of-absolute-difference (MSAD) processing as described in U.S. patent application ser. No. 09/345,244, filed Jun. 30, 1999. Successive images are coupled to the motion estimator 30 over line 56 for this purpose. The images so processed can be one, two, or three dimensional images. An example of a one dimensional image is a sample volume which is stabilized relative to a blood vessel, for instance.

The results of the motion estimation processing are coupled to an image aligner 32 by way of line 58. When the ultrasound system is to produce stabilized images the image aligner uses the estimated motion, which could be in the form of a cross-correlation coefficient of time-successive images analyzed by the MSAD process, to align the anatomy in the successive images. The result is that the image will appear to the clinician to be stable on the display screen, without undesired movement or jitter. The image aligner receives the time-successive images by way of line 62 and produces a sequence of stabilized images on line 64, which are then coupled to the video processor 24 for display. The image aligner 32 aligns successive images when commanded to do so over control line 68 from a stabilize decision processor 34. The stabilize decision processor 34 also disables the usual path for processed image signals to the video processor 24 as symbolized by the switch 76 which is controlled by a control line 66, so that the video signals processed for display are the stabilized signals produced by the image aligner which are present on line 64.

Figure 2A:
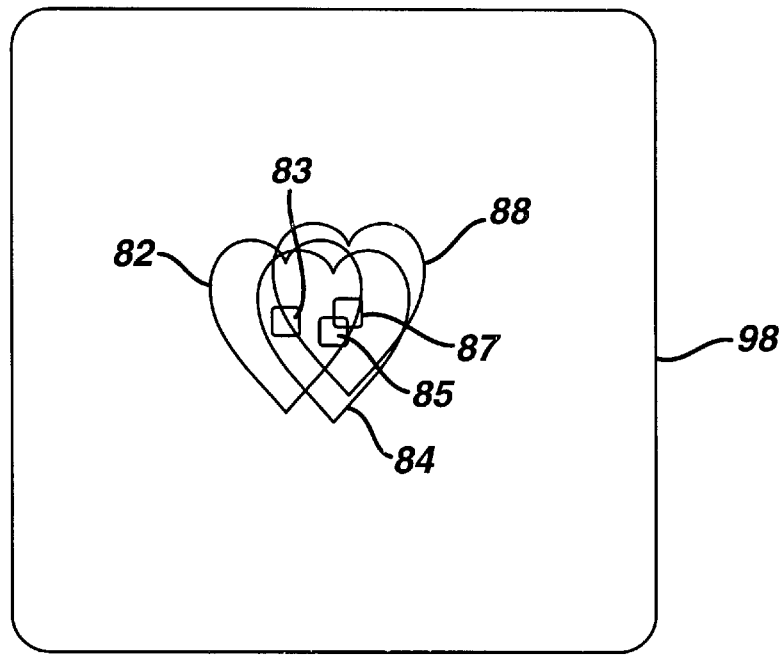
FIGS. 2a and 2b illustrate the stabilization of an ultrasound image.
Figure 2B:
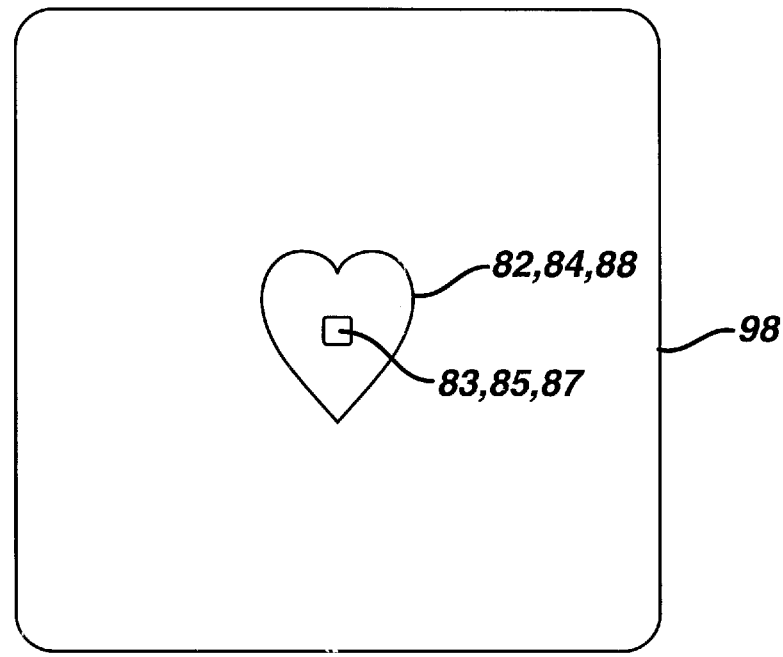

The principle of ultrasound image stabilization is illustrated in FIGS. 2a and 2b. FIG. 2a illustrates three images 82, 84, 88 of the heart, which are acquired as either the probe or the heart are moving. The images would be successively displayed in time, but for purposes of illustration are shown together in an overlapping drawing. If the probe is moving as the images are acquired, which may be the case with an uncooperative patient, the heart may appear in the position shown at 82 at one time, then in the next image may appear in the position shown at 84, and at a still later time may appear in the position shown at 88. Alternatively, the heart may be moving around as it is beating and thus appear in a different location in the transducer aperture 98 each time a new real time image is acquired. The heart will appear under either condition to jitter or jump from one position to another as these images are successively displayed in real time. If the clinician is trying to diagnose the performance at a specific location in the heart, such as a heart valve indicated symbolically by box 83 in one heart image, box 85 in the next image, and box 87 in the third image, such diagnosis will be nearly impossible as this small portion of the image jumps around on the screen. The clinician can attempt to overcome the problem by pressing the "Freeze" button on the ultrasound system control panel 40, in the hope that the frozen image will contain a clear display of the anatomy in question. This may or may not be the case, and in any event is dependent upon luck rather than diagnostic expertise. Furthermore, the clinician may be interested in evaluating the dynamic characteristic of anatomy such as a heart valve, which cannot be done with a single frozen image.

An embodiment of the present invention attempts to eliminate the jumping or jitter or blurring of such images by consistently displaying the same anatomy in the same place on the display screen. When the image aligner is successfully aligning the anatomy of the successive images each successive image will be displayed in alignment with the position of the same anatomy in the previous image. The appearance to the clinician will be that the anatomy is remaining stationary or moving without jitter on the screen. This is depicted in FIG. 2b, where each successive image 82, 84, 88 of the heart is displayed in the same position as the previous heart image, with the heart valve located in the same position 83, 85, 87 in the successive images. This effectively removes the jitter or jumpiness in the real time image display. The clinician may thus be able to make a reliable diagnosis from the stabilized images, or can reliably press the "Freeze" button when the desired anatomy is pictured in the stabilized image. When a dynamic characteristic of the anatomy is being evaluated, a sequence of real time images is captured and stored in a Cineloop® memory, the anatomy in the image is aligned, and the stabilized sequence replayed as a stabilized real time sequence. Review of the stabilized sequence in the Cineloop memory will then allow evaluation of a dynamic characteristic such as the action of a heart valve.

Figures 3, 4:
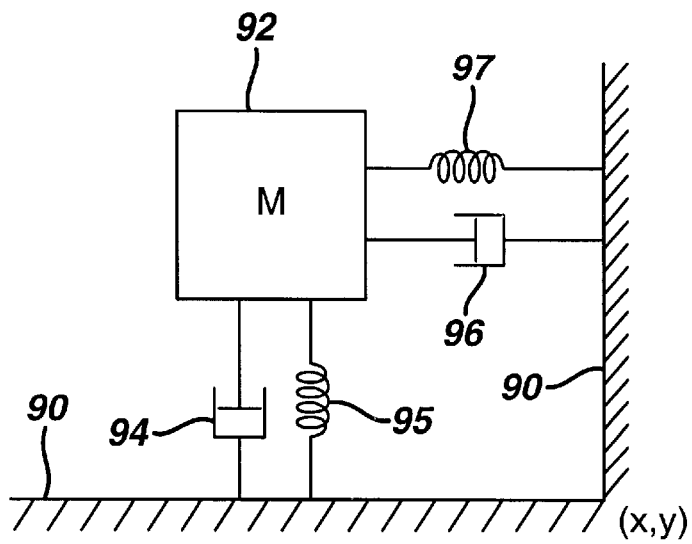
FIG. 3 illustrates the principle of image stabilization by a mechanical equivalent.
FIG. 4 illustrates a decision table by which an embodiment of the present invention acts to remain in or terminate the stabilization mode of operation.

FIG. 3 depicts a mechanical analogy to the operation of an image stabilization system of the present invention. In this drawing a mass 92 is shown in relation to a foundation or base 90. The (x,y) coordinates of the base are equivalent to the coordinates of the current image. The coordinates of the mass 92 represent the coordinates of the stabilized image, the mass, which is to be stably located in relation to the base. In this case any translation of the mass 92 in relation to the base is damped by springs 95,97 and dashpots 94,96, which represent motion stabilizing elements. The detected motion and velocities of the images (mass) are then used to calculate the position of the mass 92 in relation to the base 90. In this way a real time stabilized image sequence is obtained by using the coordinates of the mass as the reference for stabilization.

The stabilize decision processor 34 of FIG. 1 operates to intelligently decide when to attempt to stabilize images for probe or anatomy motion, and when to inhibit such attempts. Inhibiting includes not only stopping the stabilization process, but also preventing the display of images on which stabilization has been attempted. The stabilize decision processor 34 can operate either by manual or automatic, adaptive control. For example, the clinician may be operating the ultrasound system in a survey mode, where the clinician is trying to locate anatomy of interest. While doing so, the clinician may set a control on the control panel 40 to "Survey Mode." When the ultrasound system is in the survey mode, the stabilize decision processor 34 will not make any attempts to stabilize the image, since the clinician desires to see a constantly changing view of the interior of the body as the clinician searches for anatomy of interest. The control lines 66,68 from the stabilize decision processor 34 will then disable the image aligner 32 from attempting to align successive images, and will effectively close switch 76, enabling the normal succession of real time images to proceed from the image processor 20 to the video processor 24.

While in the survey mode, the clinician may spot an anatomical feature in the image which the clinician wants to examine in some detail. The clinician will then stop moving the probe so that the feature of interest remains continuously in the image field, and will set the control panel to the "Target Mode" of operation. In the target mode the ultrasound system will attempt to stabilize the image so that the anatomical feature of interest will remain stationary in the image. The image aligner 32 will be commanded to begin stabilizing successive images, and the switch 76 will effectively be opened so that the flow of stabilized images from the image aligner 32 will appear on the display screen 26.

Rather than rely upon manual activation of image stabilization as just described, the stabilize decision processor 34 may adaptively determine when to start and stop attempts at image stabilization. The stabilize decision processor does this by processing the information received on its input lines as shown in FIG. 1 and making decisions based upon the received information as illustrated by the decision table of FIG. 4. In the case of the survey and target modes just discussed, when the clinician is moving the probe rapidly or over large distances across the body, this activity may be detected in several ways. This probe motion may be estimated by a probe motion sensor and communicated to the motion estimator over line 52, or it may be estimated by significant motion artifacts in the image, or by a strong Doppler signal from image to image, or by a zero or near-zero cross-correlation of the content of one image to another as different anatomy enters and then leaves the image. This motion information is communicated to the stabilize decision processor 34 over line 74. The stabilize decision processor will then conclude that the probe or anatomy in the image has moved a large distance or that the probe or anatomy is moving quickly. Under these conditions image stabilization will not start, or will unlock (be inhibited) if stabilization was previously engaged.

On the other hand, when the clinician locates some anatomy of interest, the motion of the probe will virtually stop as the clinician focuses on the anatomy in the image. The only motion will be that of the probe or anatomy in which the anatomy moves slowly and only appears to move a short distance. This can be undesired motion of the probe due to an uncooperative patient, patient breathing, or the natural motion of an organ such as the heart. When this slow motion over short distances is detected by the motion sensors, the stabilize decision processor 34 will activate the stabilization process through control lines 66,68, or will cause the previously activated stabilization processing to remain locked in an operating state.

If the clinician finishes the diagnosis of one part of anatomy and begins to search for another feature of interest, the probe or anatomy in the image will begin to move slowly over a significant distance and new anatomy enters and then leaves the image aperture of the probe. When this condition is detected the stabilize decision processor 34 responds by unlocking the stabilization processing so the clinician can again begin to survey the anatomy. Attempts to align anatomy which moves into and then out of the field of view will be unavailing, as any feature which is being maintained in the image will soon disappear from view and not be available for subsequent alignment.

The decision table of FIG. 4 illustrates some decision criteria based upon image processing. One is that the motion of only a few pixels in an image from one image frame to another will result in a decision that-the stabilization process stay locked and continue to operate. An example of such a condition is imaging of the heart, where the heart may remain stable and stationary in the image but the valves will be seen opening and closing. This motion of the valves will cause the pixels where the valves appear to change significantly in the small area of the image where they are located, but the pixels displaying the rest of the heart may remain relatively stationary from one frame to another and only move as the heart beats. When the stabilize decision processor 34 detects this condition it assumes that the clinician is attempting to hold the probe steady and will stabilize the beating heart in the same area of the image. The gross motion or swinging of the heart will be removed if possible during the stabilization process, but no attempt will be made to compensate for localized motion such as the changing shape of the heart as it beats and the motion of the heart valves as they open and close.

Another condition shown in the decision table is that in which many pixels in the image move from frame to frame. This is another condition that can be detected by image processing such as MSAD processing. When many pixels in the image move, a condition of global motion, it is generally because the clinician is looking for different anatomy, particularly if the condition persists for several frames or repetitively in the same direction. Under these conditions the stabilize decision processor 34 will cause the stabilization process to be unlocked. However, it may be desirable to remove jitter when the clinician is moving the probe in a "survey" mode, as described below. The decision is shown with an asterisk in the table of FIG. 4, because a short, sudden movement of many pixels in the image may be due to a reflexive movement by the clinician or an uncooperative patient. Hence the stabilize decision processor 34 may conclude, for momentary movements of many pixels, to continue to stay locked in the stabilization mode until a longer term effect is registered.

The table of FIG. 4 also shows a condition of a poor registration coefficient resulting from registration processing of successive images such as MSAD processing. A poor registration coefficient would arise, for instance, when the probe moves in the elevation direction relative to a two dimensional image, or in-plane motion occurs over a large distance. These are conditions where it would be difficult if not impossible to maintain stabilization, hence the usual response to a poor registration coefficient is to unlock or inhibit stabilization operation.

Figure 5:
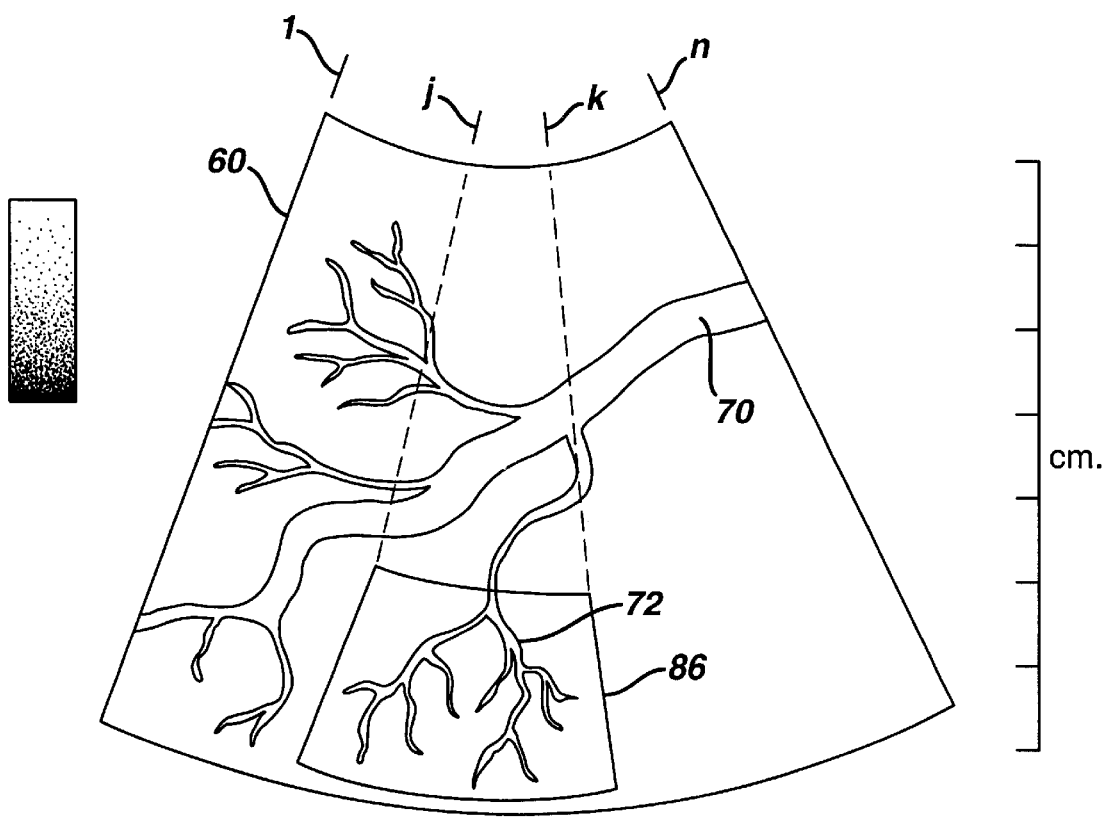
FIG. 5 illustrates an ultrasound image with a box delineating a region of interest.

A feature of ultrasonic imaging which is greatly enhanced by an embodiment of the present invention is the "zoom" feature, in which a feature found in a wide view image is enlarged for more detailed analysis. FIG. 5 illustrates an ultrasound image 60 showing a blood vessel 70. Generally such an image is displayed as a color flow image, in which the blood flow velocity or intensity in the vessel 70 is displayed in color. In this example a branch 72 of the blood vessel 70 is targeted by the clinician for more detailed examination. A region of interest (ROI) in the image which contains the branch 72 is delineated by a box 86. The branch 72 is enlarged or zoomed by displaying the anatomy in the box 86 in an enlarged view of the same size as the full image 60. This may be done by remapping the pixels in the box 86 to a larger display map, in which the zoomed ROI is shown as a full size image. It is desirable when zooming an image to stabilize the anatomy in the ROI box when zoomed, to enable the clinician to conduct a detailed evaluation of the anatomy. One way to do this in accordance with the principles of the present invention is to note that the full image 60 may be scanned by n scanlines, of which the edge scanlines 1 and n are labeled at the top of the image 60. The ROI box 86 is scanned only by scanlines j through k of the n scanlines. However, if the anatomy 72 or the imaging probe move, the ROI box will be within the field of view of a different set of scanlines. For example, if the box 86 would move the distance of two scanlines to the left, it would be scanned by scanlines j-2 to k-2. The stabilization system of FIG. 1 reacts to this movement by issuing a command over line 78 to the beamformer to scan the ROI with scanlines j-2 through k-2, or by a command to the image processor to zoom the ROI within the lateral span of scanlines j-2 through k-2. In either case, stabilization is performed on the anatomy within the ROI box 86.

Another approach to the problem of a moving ROI box is to track the motion of the anatomy, then for the ultrasound system to move the ROI box 86 in synchronism with the anatomical or probe motion. This will keep the vessel 72 constantly located in the ROI box 86 even as the entire image moves. This will maintain the integrity of quantified measurement being made over time on the anatomy within the ROI box, for instance.

When an elevation dimension is present in the image data set, as is the case with three dimensional imaging, motion in all three directions can be analyzed to track anatomy of interest and maintain a lock on stabilization of the anatomy. In the simple case of three image planes which are in adjacent, parallel image planes, the displayed plane would generally be the central one, which is in the center of the elevation aperture. But if motion occurred in the elevation dimension so that the anatomy being displayed moved into the adjacent elevation plane, image stabilization can still be performed by using the adjacent elevation plane as the displayed image. It will be appreciated that a two dimensional array will enable the ultrasound system to track motion in the elevation dimension from one plane to another. This capability also enables a multiplanar reformatted (MPR) plane, which is a plane synthesized from a 3D data set, to be tracked as anatomy of interest moves from MPR plane to another. As the anatomy moves to a different MPR plane, a new set of planar coordinates are used for the MPR image, enabling the anatomy to remain stationary on the display screen even in the presence of motion. In the correlation used to follow in-plane motion, the cross-correlation coefficient of frame to frame correlation is generally used for stabilization. When motion is tracked in the elevation dimension as opposed to the in-plane dimension, use of frame to frame decorrelation will often be the preferred indicator for stabilization decision-making.

The motion estimated by the motion estimator 30 for image stabilization can be used for other purposes. The detected motion can be supplied to the flash suppression algorithm, for instance, to improve the robustness of the performance of the algorithm. Images which are stabilized in accordance with the present invention will generally exhibit improved persistence processing, which usually involves some form of temporal averaging. With spatial coordinates maintained over a temporal sequence of images, persistence algorithms can perform better, such as that shown in U.S. Pat. No. 5,215,094, in which peak flow velocity is temporally sustained.

As mentioned previously, it may at times be useful to take out the "jitter" in the image while the probe is being intentionally moved along the body, while allowing the desired movement of the view to continue. The undesired jitter is often characterized by relatively high frequency, short duration motion, and can be distinguished on that basis. In accordance with a further aspect of the present invention, real time imaging is stabilized in the presence of jitter by estimating the translation between successive images in the x and y directions. The velocity of movement in both directions may also be estimated, which is the ratio of the translation in the given direction divided by the inter-frame time interval. The translation of the current and previous image in each direction is then taken in combination with the translations between a number N of previous images, such as 10–15 images, and are effectively low pass filtered to produce a filtered translation value in each direction for the current image relative to the previous image. Low pass filtering can be performed by a digital filter such as a Butterworth filter with a cutoff frequency below that of high frequency motion (jitter) which is undesired. Low pass filtering can also be accomplished by integrating the cumulative motion of the N previous images, by an averaging process, or by an inertial filter as modeled in FIG. 3. The inertial filter would use the velocity estimates referred to above. A reference point in the current image is determined in relation to the pixel origin, corner of the image, or other identified reference point, and the new image is warped or translated to the new reference point in accordance with the filtered translation value. This filtered translation value will be substantially representative of the intentional movement of the probe by the user, but will be damped by the filtering process to reduce motion due to unwanted image jitter. If persistence is being used, the previous frames used in the persistence calculation should also be aligned to the current image for successful operation of the persistence algorithm. As a probe is being moved across the surface of the body, most of the intentional motion resulting from movement of the probe will be in the x direction, with little intentional motion in the y direction. This fact can be taken into consideration in choosing the time constants or cutoffs for the filtering process, with a lesser time constant or lower frequency cutoff being used in the y direction filtering process than that used in the x direction filtering process. If desired, a maximum limit in frame-to-frame translation can be set, and translations with estimates which exceed the limit are constrained to the limit value.

What is claimed is:

1. An ultrasonic diagnostic imaging system with image stabilization comprising:

an ultrasonic probe which images anatomy within a field of view;

a beamformer coupled to the ultrasonic probe;

an image processor coupled to the beamformer;

an image display coupled to the image processor;

a motion estimator which estimates at least one of probe motion and anatomy motion; and a stabilize decision processor, responsive to at least one of the probe motion estimator and the anatomy motion estimator, which determines whether to maintain or end image stabilization.

2. The ultrasonic diagnostic imaging system of claim 1, wherein the image processor includes an image aligner, responsive to the motion estimator, which aligns the anatomy of temporally different images, wherein the anatomically aligned images are successively displayed on the image display as a stabilized image.

3. The ultrasonic diagnostic imaging system of claim 1, wherein the motion estimator estimates motion by image processing two temporally different images.

4. The ultrasonic diagnostic imaging system of claim 3, wherein the motion estimator performs at least one of MSAD analysis, feature matching, mutual information, correlation, and normalized correlation.

5. The ultrasonic diagnostic imaging system of claim 1, wherein the stabilize decision processor inhibits image stabilization when the probe or the anatomy move a large distance.

6. The ultrasonic diagnostic imaging system of claim 1, wherein the stabilize decision processor inhibits image stabilization when the probe or the anatomy move quickly.

7. The ultrasonic diagnostic imaging system of claim 1, wherein the stabilize decision processor does not inhibit stabilization when the probe or the anatomy moves slowly a short distance.

8. The ultrasonic diagnostic imaging system of claim 1, wherein the stabilize decision processor inhibits image stabilization when the probe or the anatomy moves slowly a long distance.

9. The ultrasonic diagnostic imaging system of claim 1, wherein the stabilize decision processor does not inhibit stabilization when only a few pixels in an image move.

10. The ultrasonic diagnostic imaging system of claim 1, wherein the stabilize decision processor inhibits image stabilization when many pixels in an image move.

11. The ultrasonic diagnostic imaging system of claim 1, wherein the stabilize decision processor inhibits image stabilization when there is a poor correlation resulting from the comparison of temporally different images.

12. The ultrasonic diagnostic imaging system of claim 1, further comprising a user interface by which a user manually sets an operating condition, wherein the stabilize decision processor is responsive to the setting of the operating condition.

13. The ultrasonic diagnostic imaging system of claim 1, further comprising a graphic display, coupled to the image display, by which a user delineates a region of interest, wherein the stabilize decision processor causes the image of the anatomy within the region of interest to be stabilized.

14. The ultrasonic diagnostic imaging system of claim 13, wherein the stabilize decision processor is coupled to the beamformer to cause the image of the anatomy within the region of interest to be stabilized.

15. The ultrasonic diagnostic imaging system of claim 13, wherein the stabilize decision processor is coupled to the image processor to cause the image of the anatomy within the region of interest to be stabilized by image processing.

16. A method for stabilizing an ultrasonic image display comprising:

receiving a first real time ultrasound image;

receiving a second real time ultrasound image which is temporally different from the first image;

estimating at least one of probe or anatomical motion occurring between the first and second images;

anatomically aligning the first and second images; and successively displaying the anatomically aligned images.

17. The method of claim 16, wherein estimating comprises correlating the first and second images.

18. The method of claim 17, wherein correlating comprises performing frame to frame correlation in the plane of a two dimensional image.

19. The method of claim 17, wherein correlating comprises performing frame to frame correlation in the elevation dimension.

20. The method of claim 16, wherein estimating comprises sensing probe motion between the first and second images.

21. The method of claim 16, wherein successively displaying comprises displaying a zoomed image in real time.

22. The method of claim 16, wherein anatomically aligning comprises following a region of interest with different scanlines of an ultrasound probe.

23. The method of claim 16, wherein anatomically aligning comprises keeping displayed anatomy within a delineated region of interest.

24. The method of claim 16, further comprising processing the first and second images with a persistence algorithm.

25. A method for stabilizing an ultrasonic image display of ultrasonic real time images produced by a moving ultrasound probe comprising:

acquiring a sequence of ultrasonic real time images;

estimating the motion between successive ones of the real time images to produce a plurality of motion estimates;

filtering the motion estimates to produce a filtered estimate value; and utilizing the filtered estimate value to translate a recent real time image relative to a previous real time image of the sequence.

26. The method of claim 25, wherein estimating comprises estimating the motion between successive ones of the real time images in at least two dimensions.

27. The method of claim 26, wherein filtering comprises filtering the motion estimates in at least two dimension using at least one of a different filter time constant and a different filter cutoff for each dimension.

28. The method of claim 25, wherein filtering comprises filtering the motion estimates by one of a low pass filter, Butterworth filter, integration process, inertial filter or averaging process.

29. The method of claim 25, wherein utilizing comprises reducing undesired image jitter relative to intentional movement of the ultrasound probe.

* * * * *